United States Patent
Spadaro et al.

(10) Patent No.: US 11,744,962 B2
(45) Date of Patent: Sep. 5, 2023

(54) INHALER WITH COMPOSITE POROUS SUPPORT ELEMENT

(71) Applicant: PHILIP MORRIS PRODUCTS S.A., Neuchâtel (CH)

(72) Inventors: Fabiana Spadaro, Lausanne (CH); Gianpaolo D'Ambra, Castel Maggiore (IT); Silvia Capo, Capaccio-Paestum (IT)

(73) Assignee: Philip Morris Products S.A., Neuchâtel (CH)

( * ) Notice: Subject to any disclaimer, the term of this patent is extended or adjusted under 35 U.S.C. 154(b) by 479 days.

(21) Appl. No.: 17/040,793

(22) PCT Filed: Mar. 26, 2019

(86) PCT No.: PCT/IB2019/052446
§ 371 (c)(1),
(2) Date: Sep. 23, 2020

(87) PCT Pub. No.: WO2019/186395
PCT Pub. Date: Oct. 3, 2019

(65) Prior Publication Data
US 2021/0052832 A1    Feb. 25, 2021

(30) Foreign Application Priority Data

Mar. 26, 2018  (EP) .................................... 18164078

(51) Int. Cl.
*A24F 42/20*   (2020.01)
*A24F 42/60*   (2020.01)
(Continued)

(52) U.S. Cl.
CPC ........... *A61M 15/003* (2014.02); *A24F 42/20* (2020.01); *A24F 42/60* (2020.01);
(Continued)

(58) Field of Classification Search
None
See application file for complete search history.

(56) References Cited

U.S. PATENT DOCUMENTS

| 6,772,755 B2 | 8/2004 | Pera |
| 8,646,461 B2 * | 2/2014 | von Borstel ............ A61P 43/00 131/273 |

(Continued)

FOREIGN PATENT DOCUMENTS

| AR | 101938 A * | 1/2017 | ............... A24B 3/14 |
| AR | 101938 A1 * | 1/2017 | ............... A24B 3/14 |

(Continued)

OTHER PUBLICATIONS

Extended European Search Report for EP Application No. 18164078.0, issued by the European Patent Office; dated Sep. 21, 2018; 10 pgs.
(Continued)

*Primary Examiner* — Russell E Sparks
(74) *Attorney, Agent, or Firm* — Mueting Raasch Group

(57) ABSTRACT

An inhaler article includes a body (110) extending along a longitudinal axis from a mouthpiece (112) end to a distal end with an endpiece element at the distal end (114). A capsule cavity is defined within the body. An air inlet region is between the endpiece element (120) and the capsule cavity (116). A composite porous support element (140) defines a downstream end of the capsule cavity. The composite porous support element is formed of a first porous material concentrically disposed about a second porous material. The first porous material has a first resistance to draw and the second porous material having a second resistance to draw. The first resistance to draw is different than the second resistance to draw. A mouthpiece air channel (113) extends from the capsule cavity, through the composite porous element to the mouthpiece end.

20 Claims, 2 Drawing Sheets

Figure 1:
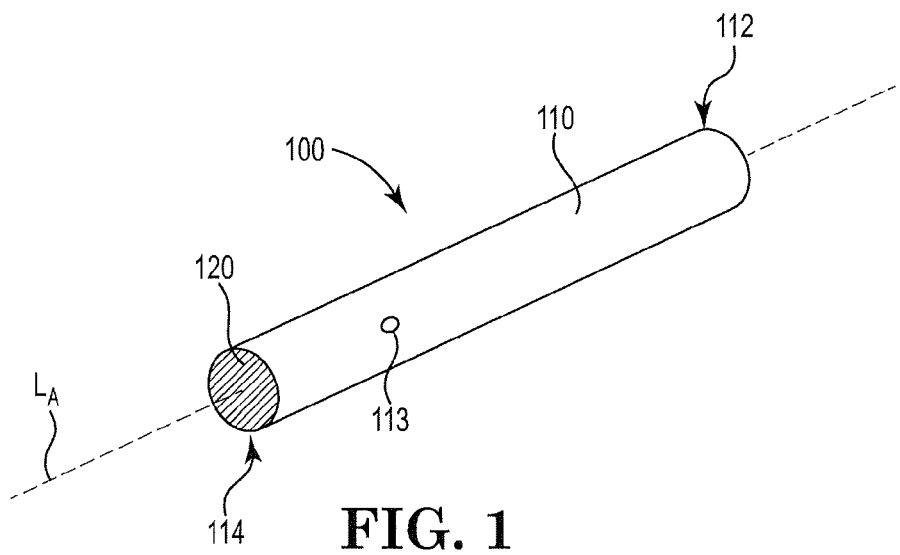
Figure 2:
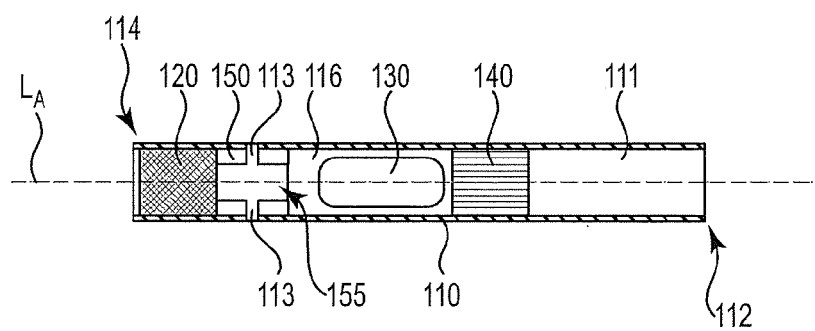
Figure 3:
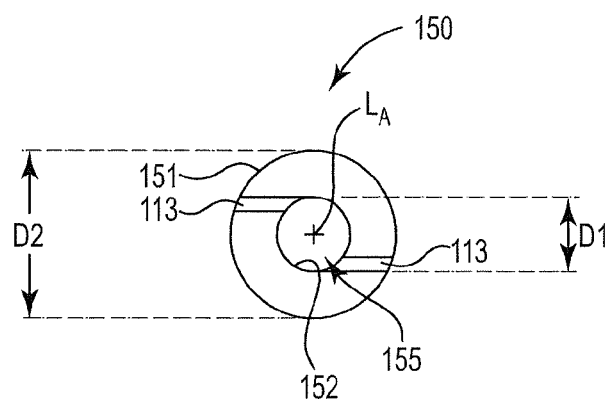

(51) Int. Cl.
A61M 15/00 (2006.01)
A61M 15/06 (2006.01)

(52) U.S. Cl.
CPC ........ *A61M 15/0021* (2014.02); *A61M 15/06* (2013.01); *A61M 2202/064* (2013.01); *A61M 2206/16* (2013.01)

(56) References Cited

U.S. PATENT DOCUMENTS

| | | | |
|---|---|---|---|
| 10,206,427 B2* | 2/2019 | Pijnenburg | ............. A24B 15/16 |
| 10,842,954 B2* | 11/2020 | Reevell | ................. A24F 40/485 |
| 2002/0121277 A1 | 9/2002 | Pera | |
| 2017/0340015 A1 | 11/2017 | Thorens | |

FOREIGN PATENT DOCUMENTS

| | | | |
|---|---|---|---|
| EP | 2399637 A1 | 12/2011 | |
| EP | 2606752 A1 | 6/2013 | |
| EP | 2893820 A1 | 7/2015 | |
| JP | H11318421 A | 11/1999 | |
| RU | 2673611 | 11/2018 | |
| WO | 20110110970 A9 | 9/2011 | |
| WO | WO 2010/095659 A1 | 8/2012 | |
| WO | WO 2012/023515 A1 | 10/2013 | |
| WO | 20150193498 | 12/2015 | |
| WO | WO 2016/203362 A1 | 12/2016 | |
| WO | WO 2014/080516 A1 | 1/2017 | |
| WO | 20170109626 A1 | 6/2017 | |
| WO | WO 2017/109678 A1 | 6/2017 | |
| WO | WO 2018/007887 A1 | 1/2018 | |

OTHER PUBLICATIONS

International Search Report for PCT/IB2019/052446, issued by the European Patent Office; dated Jun. 17, 2019; 10 pgs.
International Preliminary Report on Patentabilty for PCT/IB2019/052446, issued by the European Patent Office; dated Jun. 8, 2020; 11 pgs.
Cohen et al., "GRAS Flavoring Substances," 27. *GRAS Flavoring Substances. Food Technology for Flavoring Extract Manufacturers Association*, Aug. 2015:69(8):40-59.
Hall, R.L. & Oser, B.L., "Recent Progress in the Consideration of Flavoring Ingredients under the Food Additive Amendments 3. GRAS substances," *Food Technology*, Feb. 1965: p. 151-197.
Russian Office Action for RU Application No. 2020131564, issued by the Patent Office of the Russian Federation, dated May 23, 2022; 20 pgs. including English translation.
First Office Action for Chinese Application No. 201980017128.X issued by the China National Intellectual Property Administration dated Feb. 28, 2022; 17 pgs. including an English translation.
Japanese Office Action for JP 2020-544655 issued by the Japanese Patent Office dated Feb. 20, 2023, 9 pgs. Including English Translation.

* cited by examiner

INHALER WITH COMPOSITE POROUS SUPPORT ELEMENT

This application is the § 371 U.S. National Stage of International Application No. PCT/IB2019/052446, filed 26 Mar. 2019, which claims the benefit of European Application No. 18164078.0, filed 26 Mar. 2018, the disclosures of which are incorporated by reference herein in their entireties.

This disclosure relates to an inhaler article that includes a composite porous support element.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose in a single breath. In addition, these complex dry powder inhalers are difficult to or produce at high speeds.

It would be desirable to provide an inhaler article that is formed of materials that form current cigarette configurations. It would be desirable to provide an inhaler article that may be assembled at high speeds. It would also be desirable to provide an inhaler article that has a form that is easy to hold and is familiar to a user, similar to a conventional cigarette. It would also be desirable to provide an inhaler article that is convenient to use by a consumer.

Various aspects of the disclosure relate to an inhaler article having a composite porous support element downstream of the capsule cavity and defining a proximal end of the capsule cavity. The composite porous support element is configured to confine and support a capsule at the proximal end of the capsule cavity during inhalation and rotation of the capsule. The porous composite support element is formed of two different porous materials that allow dry particles from the capsule to pass efficiently through the composite porous support element during inhalations. The composite porous support element may be formed of a recyclable and environmentally friendly material.

In one aspect of the disclosure, an inhaler article includes a body extending along a longitudinal axis from a mouthpiece end to a distal end with an endpiece element at the distal end. A capsule cavity is defined within the body and extends along the longitudinal axis a cavity length. An air inlet region is between the endpiece element and the capsule cavity. The air inlet region has an air inlet and an air passageway extending from the air inlet to the capsule cavity. A composite porous support element defines a downstream end of the capsule cavity. The composite porous support element is formed of a first porous material concentrically disposed about a second porous material. The composite porous support element extends along a longitudinal axis a length. The first porous material has a first resistance to draw and the second porous material having a second resistance to draw. The first resistance to draw is different than the second resistance to draw. A mouthpiece air channel extends from the capsule cavity, through the composite porous element to the mouthpiece end.

In another aspect of the disclosure, an inhaler system includes, the inhaler article described herein, and a capsule disposed within the capsule cavity of the inhaler article. The capsule contains particles having a mass median aerodynamic diameter of about 15 micrometres or less, about 10 micrometres or less, about 5 micrometres or less, or in a range from about 0.5 micrometres to about 15 micrometres, or in a range from about 1 micrometres to about 10 micrometres, or in a range from about 5 micrometres to about 10 micrometres.

In one or more aspects, the first porous material is formed of a polylactic acid material and the second porous material is formed of a cellulose acetate material. The first porous material may have a resistance to draw in a range from about 1 mm water to about 3 mm water and the second porous material may have a resistance to draw in a range from about 10 mm water to about 50 mm water (under ISO regime: 17.5 ml/sec).

In one or more aspects, the second porous material forms a central core portion and the first porous material forms an outer periphery layer circumscribed about the central core portion, the central core portion forms greater than about 50% of the diameter of the outer periphery layer. The central core portion may be formed of polylactic acid material and the outer periphery layer may be formed of cellulose acetate material. The outer periphery layer may include two or more apertures extending the length of the composite porous support element.

The endpiece element may substantially prevent or inhibit air from entering the inhaler article from the distal end. In some embodiments, the endpiece element may prevent air from entering the inhaler article through the distal end.

In one or more aspects, the air inlet region induces a vortex of inhalation air airflow into the capsule cavity. The helical features may be aligned with the air inlets of the air inlet region.

In one or more aspects, the mouthpiece air channel and composite porous element may be contained within a first body portion of the inhaler article, and the capsule cavity, air inlet region and endpiece may be contained within a second body portion of the inhaler article. The first body portion may be in serial axial alignment with the second body portion. A wrapper may overlay and join the first body portion to the second body portion.

In one or more aspects, the body of the inhaler article has an outer diameter that may be substantially constant from the distal end to the mouthpiece end. The outer diameter of the body may be in a range from about 6 mm to about 10 mm, or from about 7 mm to about 8 mm.

In one or more aspects, the endpiece may extend longitudinally along the longitudinal axis of the body of the inhaler article. The endpiece may have a length in a range from about 5 mm to about 10 mm, and the vortex tunnel may extend longitudinally along the longitudinal axis of the body a length in a range from about 5 mm to about 10 mm.

In one or more aspects, the system may include a capsule containing particles comprising nicotine.

In one or more aspects, the system may include a capsule further containing a second population of flavor particles.

In one or more aspects, the system may further include a piercing element removably engageable with the inhaler article to activate the capsule. As used herein "activating" a capsule refers to opening a capsule, such as by piercing, to enable particles contained within the capsule to be released. The endpiece element may be configured to be pierced by the piercing element when activating the capsule.

Advantageously, the inhaler article may be formed of materials used to assemble conventional cigarettes. In addition, the inhaler article define a form similar to a conventional cigarette. This may enable high speed assembly or manufacture of the inhaler article. Advantageously, rotation of the capsule may provide a uniform entrainment of a portion or a fraction of nicotine particles from the capsule over two or more, or five or more, or ten or more inhalations or "puffs" by a consumer. Advantageously, the inhaler article may be formed of biodegradable materials.

The inhaler article described herein may provide dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler article may have a form similar to a conventional cigarette and may mimic the ritual of conventional smoking. This inhaler may be simple to manufacture and convenient to use by a consumer.

Air flow management through the capsule cavity may cause the capsule to rotate during inhalation and consumption. The capsule contains nicotine particles comprising nicotine (also referred to as "nicotine powder" or "nicotine particles") and optionally particles comprising flavour (also referred to as "flavour particles). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The phrase "resistance to draw" or "RTD" refers to the static pressure difference between the two ends of a specimen when it is traversed by an air flow under steady conditions in which the volumetric flow is 17.5 milliliters per second at the output end. The RTD of a specimen can be measured using the method set out in ISO Standard 6565: 2002.

The term "porous" refers to a material containing pores. In particular, "porous" refers to a non-woven fiber material that if formed of a fiber matrix defining pores.

The term "aperture" refers to a macro void that is defined by bulk porous material.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R.L. & Oser, B.L., Food Technology, February 1965 pg. 151-197, and in the GRAS flavoring substances 27 S.M. Cohen et al., Food Technology August 2015 pg. 40-59, and intervening GRAS Flavoring Substances publications 4 to 26. For the purpose of this disclosure, nicotine is not considered as a flavourant or flavour.

The inhaler article described herein may be combined with a piercing element or piercing device to deliver the nicotine particles to a consumer. The piercing element or piercing device may be separated from or not form a portion of the inhaler article. A plurality of these inhaler articles may be combined with a piercing element or piercing device to form a kit.

An inhaler article, according to the disclosure, includes a body extending along a longitudinal axis from a mouthpiece end to a distal end. An endpiece element is located at the distal end. A capsule cavity is defined within the body and extends along the longitudinal axis a cavity length. An air inlet region is between the endpiece element and the capsule cavity. The air inlet region has an air inlet and an air passageway extending from the air inlet to the capsule cavity. A composite porous support element defines a downstream end of the capsule cavity. The composite porous support element is formed of a first porous material concentrically disposed about a second porous material. The composite porous support element extends along a longitudinal axis a length. The first porous material has a first resistance to draw and the second porous material having a second resistance to draw. The first resistance to draw is different than the second resistance to draw. A mouthpiece air channel extends from the capsule cavity, through the composite porous element to the mouthpiece end.

The body of the inhaler article, or the "inhaler body", may have any suitable shape. The inhaler body may be elongate. In other words, the inhaler body may have a length that is substantially greater than the other dimensions of the inhaler body. The inhaler body may have a substantially uniform outer diameter along its length. The inhaler body may have any suitable transverse cross-sectional shape. For example, the transverse cross-section may be circular, elliptical, square or rectangular. The inhaler body may have a circular cross-section that may be uniform along the length of the inhaler body, forming an elongated cylindrical body.

The body of the inhaler article, or "inhaler body" may resemble a smoking article or conventional cigarette in size and shape. The inhaler body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body.

The inhaler body may have an outer diameter in a range from about 6 mm to about 10 mm, or from about 7 mm to about 10 mm, or about 7 mm to about 9 mm, or about 8 mm. The inhaler body may have a length (along the longitudinal axis) in a range from about 40 mm to about 100 mm, or from about 50 mm to about 80 mm, or about 60 mm to about 80 mm, or 65 mm.

The inhaler body may be formed of a polymeric or cellulosic material, or any other suitable material. The inhaler body may be formed of a biodegradable material. The inhaler body may be formed of paperboard or cardboard. The inhaler body may have a uniform thickness along its length. The inhaler body may have a thickness in a range from about 1 mm to about 2 mm.

The inhaler body may form a unitary construction where the body extends continuously from the endpiece element to the mouthpiece end. The endpiece element, air inlet region, capsule cavity (and capsule if present), composite porous element and mouthpiece air channel may be serially disposed within the inhaler body. In other words, endpiece element, air inlet region, capsule cavity (and capsule if present), composite porous element and mouthpiece air channel may be arranged end to end along the longitudinal axis of the inhaler body.

The inhaler body may be formed of two portions, a first portion and a second portion. The first portion and the second portion may be axially aligned in serial abutting relationship and joined together to form the inhaler body. A wrapper may be utilized to join the first portion and a second portion together. The wrapper may be a biodegradable material. The wrapper may be a paper wrapper.

The first portion may contain the mouthpiece or mouthpiece air channel, and composite porous element. The second portion may contain the capsule cavity (and capsule if present), air inlet region, and endpiece element.

In some embodiments, the inhaler body may be formed of three portions, or more than three portions. The three portions, or more than three portions may be axially aligned in serial abutting relationship and joined together to form the inhaler body. A wrapper may be utilized to join the three portions, or more than three portions together.

The composite porous support element is a non-woven fibre composite element that is formed of two different porous materials. The bulk porous (non-woven fibre element) materials forming the composite porous support element define an outer periphery layer circumscribing a central core portion. The central core portion forms a cylinder. The outer periphery layer may extend the length of the central core portion. The composite porous support element may be configured to enhance dry particle delivery from the capsule in the capsule cavity, across the composite porous support element, to the mouthpiece end, during each inhalation event. The composite porous support element is configured to minimize particle recirculation near or across the composite porous support element. These features may improve the delivery of the dry particles to the mouthpiece or enhance the emptying of the dry particles from the inhaler during inhalations.

The first porous material may be formed of a non-woven fibre plug of polylactic acid material and the second porous material may be formed of a non-woven fibre plug of cellulose acetate material. The plug of cellulose acetate material may have a porosity in a range from 30% to 50% and a denier in a range from about 3.4 to about 8, or from about 3.7 to about 7, or from about 4 to about 6. The plug of polylactic acid material may a porosity in a range from 60% to 90%. The polylactic acid material may have a resistance to draw in a range from about 1 mm water to about 3 mm water and the cellulose acetate material may have a resistance to draw in a range from about 10 mm water to about 50 mm water (under ISO regime: 17.5 ml/sec)

The second porous material may form a central core portion and the first porous material may form an outer periphery layer circumscribed about the central core portion. The central core portion may form greater than about 50% of the diameter of the outer periphery layer. The central core portion may be formed of polylactic acid material and the outer periphery layer may be formed of cellulose acetate material. The outer periphery layer may include two or more apertures extending the length of the composite porous support element.

The one or more apertures may be configured and placed on the outer periphery layer to enhance dry particle delivery from the capsule in the capsule cavity, across the composite porous support element, to the mouthpiece end, during each inhalation event. The apertures may be configured and placed on or within the composite porous support element to minimize particle recirculation near or across the porous support element. These features may improve the delivery of the dry particles to the mouthpiece or enhance the emptying of the dry particles from the inhaler during inhalations.

The one or more apertures may extend linearly along the longitudinal length of the composite porous support element. The one or more apertures may extend curve-linearly along the longitudinal length of the composite porous support element. The one or more apertures may extend helically along the longitudinal length of the composite porous support element, preferably along the outer periphery layer of the composite porous support element.

The composite porous support element may have a length that extends along the longitudinal axis of the inhaler body. The composite porous support element may have any suitable length, such as between about 5 mm to about 10 mm. The composite porous support element may substantially fill the inner diameter of the inhaler body (including the composite porous support element apertures). The composite porous support element may have an outer diameter sufficient to form a friction fit with the inner diameter of the inhaler body. The composite porous support element may have an outer diameter in a range from about 7 mm to about 8 mm.

An endpiece element may be disposed within the distal or endpiece end of the inhaler body. The endpiece element is configured to restrict or prevent airflow through the distal or endpiece end of the body of the inhaler article. The endpiece element is configured to encourage airflow to enter the inhaler body though air inlets along the sidewall of the body, as described below, preferentially over air flowing through the endpiece element.

Where the endpiece element permits some air to enter the inhaler body through the distal end, the endpiece element has a generally high resistance to draw (RTD). The endpiece element may have an RTD of greater than about 30 mm water, or greater than about 50 mm water, or greater than about 75 mm water, or greater than 100 mm water, or greater than 200 mm water, or in a range from 30 mm water to 100 mm water.

The endpiece element may extend longitudinally along the longitudinal axis of the inhaler body. The endpiece element may have a length in a range from about 5 mm to about 10 mm.

The endpiece element may be formed of any suitable material. For example, the endpiece element may be formed of viscose paper. The endpiece element may be formed of fibers forming a tow material, or a plug of tow material. The endpiece element may be formed of a biodegradable material. The endpiece element may be formed of cellulose or cellulose acetate. The endpiece element may be formed of an acetate tow. The endpiece element may be formed of a cellulose tow. The endpiece element may be formed of an acetate and cellulose tow. The endpiece element may be formed of cellulose and viscose paper.

The endpiece element may form a cylindrical plug of material that may fill the distal end of the inhaler article body. This cylindrical plug of material may be a tow material. The cylindrical plug of material may be cellulose or cellulose acetate materials. The cylindrical plug of material may be acetate tow. The cylindrical plug of material may be cellulose tow. The cylindrical plug of material may be an acetate and cellulose tow. The cylindrical plug of material may be cellulose and viscose paper. In one or more aspects, the endpiece element may be formed of cellulose or acetate, fibers or tow, or viscose paper.

The endpiece element may be pierceable. A piercing element such as a rigid elongate needle, may pierce the endpiece element and pass through the vortex tunnel to contact a capsule within the capsule cavity and form a hole in the capsule. Particles contained within the capsule may then exit the hole formed by the piercing element during use of the inhaler article. In some embodiments, the endpiece element may at least partially reseal once the piercing element is withdrawn from the endpiece element.

An air inlet region is positioned between the endpiece element and the capsule cavity. The air inlet region may abut the endpiece element. The air inlet region may be axially aligned and in serial arrangement with the endpiece element. The air inlet region may form an upstream or distal end or boundary of the capsule cavity.

The air inlet region may be configured to initiate a "swirling" or vortex of inhalation air into the capsule cavity. The air inlet region may include two more air inlets spaced around the circumference of the inhaler body. In one more aspects, the air inlet region includes a vortex tunnel. The vortex tunnel is configured to induce swirling or induce a vortex of inhalation airflow through the capsule cavity of the inhaler. The vortex tunnel may define an open cylinder where the air passageway extends substantially co-axially along the axis of the cylinder. The axis of this open cylinder may be co-extensive with the longitudinal axis of the inhaler article body. The vortex tunnel may extend longitudinally along the longitudinal axis of the inhaler article body a length that is greater than an inner diameter of the vortex tunnel.

The vortex tunnel may include an air inlet in fluid communication with the air passageway. The air passageway may define an inner passageway of the open cylinder. The air passageway is defined by the inner diameter or the vortex tunnel. The inner diameter of the vortex tunnel is less than an inner diameter of the inhaler body. The air inlet provides an opening for air to enter the air passageway or open cylinder from outside the inhaler article. The air inlet may extend through a sidewall (or thickness) of the vortex tunnel. In some embodiments, the air inlet extends through the body of the inhaler article. In some embodiments, the body of the inhaler article also comprises an air inlet. The air inlet of the body of the inhaler article may be aligned with the air inlet of the vortex tunnel. Where the vortex tunnel comprises more than one air inlet, the body of the inhaler article may comprise a complimentary number of air inlets, each air inlet of the inhaler body being aligned with or registered with an air inlet of the vortex tunnel.

The vortex tunnel may have an outer diameter in contact with the inner diameter of the body. The vortex tunnel may have an inner diameter in a range from about 60% to about 25% of the outer diameter of the vortex tunnel or the inner diameter of the body, or the inner diameter may be in a range from about 50% to about 35% of the outer diameter of the vortex tunnel or of the inner diameter of the body. The vortex tunnel may have a length greater than the inner diameter of the vortex tunnel. In other words, the inner diameter of the vortex tunnel may be narrow or thin relative to the outer diameter of the vortex tunnel.

The vortex tunnel may have an outer diameter substantially equal to the inner diameter of the inhaler article body. The vortex tunnel may have an inner diameter that is less than the outer diameter of a capsule disposed within the capsule cavity. The vortex tunnel may have an outer diameter of about 7 mm to about 8 mm. The vortex tunnel may have an inner diameter of about 2 mm to about 4.5 mm. or from about 3 mm to about 4 mm. The vortex tunnel may have a wall thickness in a range from about 2 mm to about 3 mm. The vortex tunnel may extend longitudinally along the longitudinal axis of the inhaler article body a length in a range from about 5 mm to about 10 mm.

The air inlet may meet or enter the air passageway of the vortex tunnel at a tangent to at least one of the surfaces (inner diameter of the vortex tunnel) and the air passageway. In particular the air inlet may extend substantially at a tangent to the axis of the inhaler body. The vortex tunnel may include two air inlets in communication with the air passageway. The vortex tunnel may include two opposing air inlets entering the open cylinder at a tangent to the inner diameter of the open cylinder. Providing one or two opposing air inlets at a tangent to the inner diameter of the open cylinder induces a swirling or vortex air flow pattern within the capsule cavity of the inhaler body.

The one or more air inlet(s) may have any suitable or useful shape. The one or more air inlet(s) may have a cylindrical shape or circular cross-section. The one or more air inlet(s) may have a diameter in a range from about 0.8 mm to about 1.2 mm, or about 1 mm. The one or more air inlet(s) may be formed by mechanical puncturing or by laser perforation.

The air inlet region or vortex tunnel may be formed of any useful material. For example, the air inlet region or vortex tunnel may be formed of cellulose acetate tow. The air inlet region or vortex tunnel may be formed of paperboard or cardboard. The air inlet region or vortex tunnel may be formed of a polymeric material.

The vortex tunnel may be constructed from a hollow cellulose acetate tube (may be referred to as "HAT"). The vortex tunnel may be formed of a hollow cellulose acetate tube or open cylinder of cellulose acetate tow. Paper may line at least one of the inner diameter and outer diameter of the vortex tunnel. The vortex tunnel may be formed of an open cylinder of cellulose acetate tow with paper lining the inner diameter. The vortex tunnel may be formed of an open cylinder of cellulose acetate tow with paper lining the outer diameter. The vortex tunnel may be formed of an open cylinder of cellulose acetate tow with paper lining both the inner diameter and outer diameter of this vortex tunnel (may be referred to as a "diffuser plug").

The capsule cavity may be immediately downstream from the air inlet region or vortex tunnel. The capsule cavity may abut the air inlet region or vortex tunnel. The capsule cavity may be axially aligned and in serial arrangement with the air inlet region or vortex tunnel. The air inlet region or vortex tunnel may form an upstream or distal end or boundary of the capsule cavity.

The capsule cavity may define a cylindrical space configured to contain a capsule. The capsule cavity may define a space configured to receive a capsule having an obround or rounded rectangular shape. The capsule cavity may have a substantially uniform or uniform diameter along the length of the capsule cavity. The capsule cavity may have a circular transverse cross-section along the length of the capsule cavity. The capsule cavity may have a cylindrical shape. The configuration of the capsule cavity relative to the capsule may allow the capsule to rotate with stability within the capsule cavity. The longitudinal axis of the capsule may rotates with stability about the longitudinal axis of the inhaler body during inhalation.

Stable rotation refers to the longitudinal axis of the inhaler body being substantially parallel with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" by a consumer.

The capsule cavity may have a fixed cavity length bounded on an upstream or distal end by the air inlet region and bounded on the downstream end by the porous support element. The capsule cavity may have a cavity length of about at least about 110% to less than about 200% of a length of the capsule contained therein, or from about 120% to about 130% of the capsule length, or about 125% of the capsule length. The cavity length may be in a range from about 15 mm to about 25 mm and the capsule length may be in a range from about 14 to about 18 mm, or the cavity length may be about 20 mm and the capsule length may be about 16 mm.

The capsule cavity has a cavity inner diameter, orthogonal to the longitudinal axis, and the capsule has a capsule outer diameter. The capsule outer diameter may be in a range from about 80% to about 99% of the cavity inner diameter, or capsule outer diameter may be in a range from about 85% to about 95% of the cavity inner diameter, or capsule outer diameter may be about 90% of the cavity inner diameter. The capsule outer diameter may be in a range from about 5.4 mm to about 6.4 mm and the cavity inner diameter may be in a range from about 6 mm to about 7 mm.

The capsule cavity may be bounded on an upstream distal side by the air inlet region and bounded on a downstream or mouthpiece side by the porous support element. The air inlet region and porous support element may cooperate to contain the capsule longitudinally within the capsule cavity. The porous support element may fill the inner diameter of the elongated inhaler body. The porous support element may allow air flow to exhibit a uniform airflow along the cross-section of the elongated inhaler body through the porous support element. The porous support element may function as a diffuser to reduce turbulence effects or edge effects and ensure or maintain the desired air flow pattern through the capsule cavity. The porous support element may support a capsule inside the capsule cavity during activation of the capsule, such as by providing a support for the capsule as a piercing element is received in the inhaler article at the distal end and pierces the capsule to activate the capsule.

A capsule may be sealed within the inhaler article prior to consumption. For transport and storage, the inhaler article may be contained within a sealed or airtight container or bag. The inhaler article may include one or more peelable seal layers to cover the one or more air inlet channels or the air outlet or mouthpiece of the inhaler article. This may ensure the inhaler articles maintain appropriate hygiene and freshness or may prevent the capsule from drying out and becoming hard or friable.

The capsule may rotate about its longitudinal or central axis when air is drawn through the inhaler article. The capsule may be formed of an airtight material that substantially contains the particles inside the capsule. The capsule may be configured to be pierced or punctured by a piercing element when the capsule is within the capsule cavity. The piercing element may be separate or combined with the inhaler article. The capsule may be formed of any suitable material. The capsule may formed of a metallic or polymeric material that serves to keep contaminants out of the capsule but may be pierced or punctured by a piercing element prior to consumption to enable the release of the nicotine particles from within the capsule. The capsule may be formed of a polymer material. The polymer material may be hydroxypropylmethylcellulose (HPMC). The capsule may be any suitable size. The capsule may be a size 1 to size 4 capsule, or a size 3 capsule, or a size 3 capsule.

The system may comprise a separate piercing element, such as a metal or rigid needle. The piercing element may form a single aperture through the capsule received in the capsule cavity. The piercing element may be configured to pass through the endpiece element and through the air passageway of the vortex tunnel into the capsule cavity. In some embodiments, the endpiece element may be resealable after the piercing element has been withdrawn from the inhaler article. In some embodiments, the inhaler article may comprise a resealable element for sealing the endpiece element after the piercing element has been withdrawn from the inhaler article.

The capsule contains a dry powder comprising pharmaceutically active particles and optionally flavour particles. The capsule may contain a predetermined amount of dry powder. The capsule may contain enough dry powder to provide at least 2 inhalations or "puffs", or at least about 5 inhalations or "puffs", or at least about 10 inhalations or "puffs". The capsule may contain enough dry powder to provide from about 5 to about 35 inhalations or "puffs", or from about 8 to about 25 inhalations or "puffs". Each inhalation or "puff" releases an approximate or substantially equal or equivalent amount of dry powder into the inhalation air stream.

The capsule may contain a dry powder about 50% to about 95% by weight pharmaceutically active particles and from 50% to 5% by weight flavour particles, or from 70% to about 90% by weight pharmaceutically active particles and from 30% to 10% by weight flavour particles. The capsule may contain from 30 mg to 70 mg of dry powder, or from 40 mg to 60 mg of dry powder.

Preferably, the capsule contains pharmaceutically active nicotine particles and flavour particles. The capsule may contain a dry powder about 50% to about 95% by weight nicotine particles and from 50% to 5% by weight flavour particles, or from 70% to about 90% by weight nicotine particles and from 30% to 10% by weight flavour particles. The capsule may contain from 30 mg to 70 mg of dry powder, or from 40 mg to 60 mg of dry powder. The nicotine particles may contain from about 1% to about 10% effective nicotine, or from about 3% to about 7% effective nicotine, or about 5% effective nicotine.

When flavour particles are blended or combined with the pharmaceutically active particles within the capsule, the flavour particles are present in an amount that provides the desired flavour to each inhalation or "puff" delivered to the user.

The pharmaceutically active particles may have any useful size distribution for inhalation delivery preferentially into the lungs of a user. The capsule may include other particles than the pharmaceutically active particles. The pharmaceutically active particles and the other particles form a powder system.

The powder system may have at least about 40% or at least about 60%, or at least about 80%, by weight of the powder system comprised in pharmaceutically active particles having a particle size of about 10 micrometres or less, or 5 micrometers or less, or in a range from about 1 micrometer to about 3 micrometres.

The powder system may have at least about 40% or at least about 60%, or at least about 80%, by weight of the powder system comprised in pharmaceutically active particles having a particle size of about 10 micrometres or less, or 5 micrometers or less, or in a range from about 1 micrometer to about 3 micrometres.

The pharmaceutically active particles may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Preferably the pharmaceutically active particle are nicotine particles. Nicotine in the powder system or nicotine particles is preferably a pharmaceutically acceptable freebase nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid is leucine such as, L-leucine. Providing an amino acid such as L-leucine with the particles comprising nicotine, may reduce adhesion forces of the particles comprising nicotine and may reduce attraction between nicotine particles and thus reduce agglomeration of nicotine particles.

Similarly, adhesion forces to particles comprising flavour is also reduced thus agglomeration of pharmaceutically active particles with flavour particles is also reduced. The powder system described herein thus may be a free-flowing material and possess a stable relative particle size of each powder component even when the pharmaceutically active particles and the flavour particles are combined.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour particles of the powder system comprised in particles having a particle size of about 20 micrometres or greater. The powder system may have at least about 40% or at least about 60%, or at least about 80%, by weight of the flavour particles of the powder system comprised in particles having a particle size of about 50 micrometres or greater. The powder system may have at least about 40% or at least about 60%, or at least about 80%, by weight of the flavour particles of the powder system comprised in particles having a particle size in a range from about 50 micrometer to about 150 micrometres. Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the pharmaceutically active or nicotine component during consumption or inhalation thereof.

Flavourants or flavours refer to a variety of flavour materials of natural or synthetic origin. They include single compounds and mixtures. The flavour or flavourant has flavour properties that may enhance the experience of the pharmaceutically active or nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, *eucalyptus*, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with pharmaceutically active or particles may also be reduced. The powder system described herein thus may possess a stable relative particle size of the particles comprising pharmaceutically active or and the particles comprising flavour even when the pharmaceutically active or particles and the flavour particles are combined. The powder system preferably free-flowing.

Conventional formulations for dry powder inhalation typically contain carrier particles that serve to increase the fluidization of the active particles since the active particles may be too small to be influenced by simple airflow through an inhaler. These powder systems typically require carrier particles. These carrier particles may be a saccharide such as lactose or mannitol that have a particle size greater than about 50 micrometres. The carrier particles may be utilized to improve dose uniformity by acting as a diluent or bulking agent in a formulation. These conventional formulations typically require high speed inhalation airflows and deglomeration elements and sieve elements to achieve a particle size that will enter the pulmonary system. Inhalation airflow boosting elements, deglomeration elements, and sieve elements add complexity and cost of the dry powder inhaler.

The powder system utilized with the dry powder inhaler of the invention may be carrier-free or substantially carrier-free. Being carrier-free or substantially carrier-free may allow the dry powder and to be inhaled and the pharmaceutically active particles be delivered to the user's lungs at inhalation or airflow rates that are similar to typical smoking regime inhalation or airflow rates. Preferably any carrier-like particles are limited to the flavour particles or flavour component of the dry power system.

The dry powder system may be combined in a single capsule. As described above, the dry powder system may each have reduced adhesion forces that result in a stable powder formulation where the particle size of each component does not substantially change when combined.

The inhaler and inhaler system may be less complex and have a simplified airflow path as compared to conventional dry powder inhalers. Advantageously, rotation of the capsule within the inhaler body aerosolizes the pharmaceutically active particles or powder system and may assist in maintaining a free-flowing powder. Thus, the inhaler article may not require the elevated inhalation rates typically utilized by conventional inhalers to deliver the pharmaceutically active particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

The dry powder utilized with the dry powder inhaler of the invention may eliminate or substantially reduce any exhalation of pharmaceutically active particles during the "exhale" phase. Preferably nearly all, or at least about 99% or at least about 95% or at least 90% of the pharmaceutically active particle has a particle size that is delivered to the lungs but are not small enough to be exhaled by tidal breathing. This pharmaceutically active particle size may be in a range from about 0.75 micrometers to about 5 micrometers, or from 0.8 micrometers to about 3 micrometers, or from 0.8 micrometers to about 2 micrometers.

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion or vortex tunnel to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 1 is a perspective view of an illustrative inhaler article.

FIG. 2 is a cross-sectional schematic diagram of the illustrative inhaler article of FIG. 1 along the longitudinal axis.

FIG. 3 is a cross-sectional schematic diagram of an illustrative air inlet region along the axial axis.

FIG. 4 is a cross-sectional schematic diagram of an illustrative composite porous support element along the axial axis.

FIG. 5 is a cross-sectional schematic diagram of another illustrative composite porous support element along the axial axis.

FIG. 6 is a cross-sectional schematic diagram of FIG. 5 with a plurality of apertures about the outer diameter.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 and FIG. 2 illustrate an exemplary inhaler article 100. FIG. 2 is a cross-sectional schematic diagram of the illustrative inhaler article 100 of FIG. 1 along the longitudinal axis $L_A$. FIG. 3 is a cross-sectional schematic diagram of the illustrative air inlet region or vortex tunnel 150 along the longitudinal axis $L_A$. The inhaler article 100 includes a body 110 extending along a longitudinal axis $L_A$ from a mouthpiece end 112 to a distal end 114 and a capsule cavity 116 defined within the body 110.

A mouthpiece air channel 111 extends from the capsule cavity 116 to the mouthpiece end 112. An endpiece element 120 is disposed within the distal end 114 and extends to a vortex tunnel 150. The endpiece element 120 is configured to restrict or prevent airflow through the endpiece element 120. In this embodiment, the endpiece element 120 is formed of a body of cellulose acetate tow, having a high resistance to draw (RTD) of at least 100 mm water per millimeter.

The air inlet region or vortex tunnel 150 is disposed within the body 110 and extends to the capsule cavity 116. The vortex tunnel 150 has an inner diameter $D_1$ defined by an inner surface 152 and an outer diameter $D_2$ defined by an outer surface 151. The inner diameter $D_1$ defined by an inner surface 152 forms an air passageway 155 in the form of an open cylinder. The vortex tunnel 150 may include two air inlets or air channels 113 extending from the vortex tunnel 150 outer surface 151 to the air passageway 155. The vortex tunnel 150 includes two air inlets 113 in communication with the air passageway 155, at opposite sides of the inhaler article 100. The two opposing air inlets 113 extend substantially linearly between the outer surface 151 of the vortex tunnel 150 and the inner surface 152, to the air passage 155 at a tangent to the inner $D_1$ diameter of the open cylinder 155. The openings of the two opposing air inlets 113 at the inner surface 152 are not aligned, and in particular, in this embodiment the two opposing air inlets 113 extend in substantially parallel directions, along axis that extend on opposite sides of the central longitudinal axis $L_A$ of the vortex tunnel 150 and the inhaler article 100. Providing two opposing air inlets 113 at a tangent to the inner diameter $D_1$ of the open cylinder 155 induces a swirling or vortex air flow pattern within the capsule cavity 116 of the inhaler body 110.

The air inlet region or vortex tunnel 150 and the composite porous support element 140 bound the capsule cavity 116. A capsule 130 may be disposed within the cavity 116. The capsule 130 contains particles comprising nicotine. The air inlet region or vortex tunnel 150 and the composite porous support element 140 cooperate to contain the capsule 130 longitudinally within the capsule cavity 116. The mouthpiece end 112 is illustrated having a recessed end where the body 110 bounds an open space at the mouthpiece end 112. Alternatively the composite porous support element 140 can extend to the mouthpiece end 112 to fill the entire mouthpiece end 112. The capsule 130 has an axis of rotation in the capsule cavity is coextensive with the longitudinal axis $L_A$.

Figure 4:
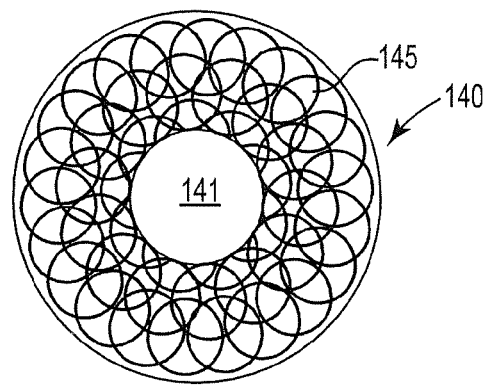

FIG. 4 is a cross-sectional schematic diagram of an illustrative composite porous support element 140 along the axial axis. A central core portion is formed of a cellulose acetate material 141. The outer periphery layer is formed from a polylactic acid material 145.

Figure 5:
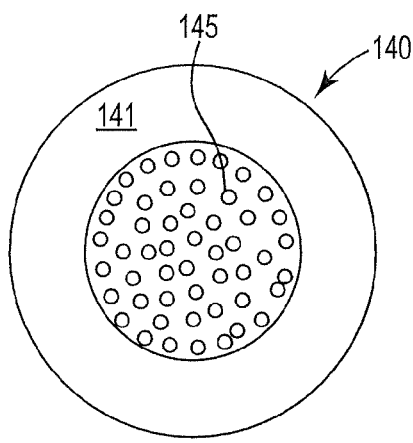

FIG. 5 is a cross-sectional schematic diagram of another illustrative composite porous support element 140 along the axial axis. A central core portion is formed of a polylactic acid material 145. The outer periphery layer is formed from a cellulose acetate material 141.

Figure 6:
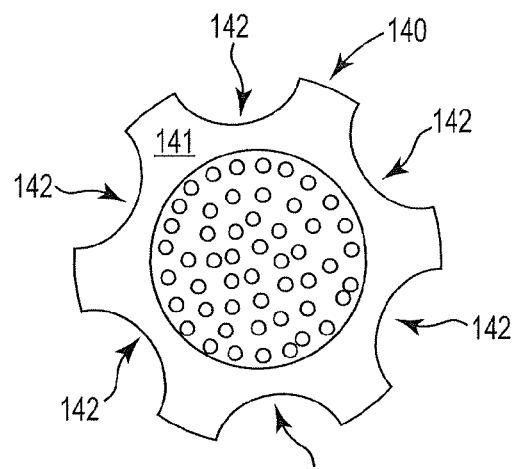

FIG. 6 is a cross-sectional schematic diagram of FIG. 5 with a plurality of apertures 142 about the outer diameter of the composite porous support element 140.

The invention claimed is:

1. An inhaler article comprising:
a body extending along a longitudinal axis from a mouthpiece end to a distal end;
an endpiece element at the distal end;
a capsule cavity defined within the body and extending along the longitudinal axis a cavity length;
an air inlet region between the endpiece element and the capsule cavity, the air inlet region having an air inlet and an air passageway extending from the air inlet to the capsule cavity;
a composite porous support element defining a downstream end of the capsule cavity, the composite porous support element formed of a first porous material concentrically disposed about a second porous material, the composite porous support element extending along a longitudinal axis a length, the first porous material having a first resistance to draw and the second porous material having a second resistance to draw, the first resistance to draw being different than the second resistance to draw, the second porous material forms a central core portion and the first porous material forms an outer periphery layer circumscribed about the central core portion, the central core portion forms a cylinder, and the outer periphery layer may extend the length of the central core portion; and
a mouthpiece air channel extending from the capsule cavity, through the composite porous element to the mouthpiece end.

2. The inhaler article according to claim 1, wherein the first porous material is formed of a polylactic acid material and the second porous material is formed of a cellulose acetate material.

3. The inhaler article according to claim 1, wherein the first porous material is formed of a cellulose acetate material and the second porous material is formed of a polylactic acid material.

4. The inhaler article according to claim 1, wherein the first porous material has a resistance to draw in a range from about 1 mm water to about 3 mm water and the second porous material has a resistance to draw in a range from about 10 mm water to about 50 mm water.

5. The inhaler article according to claim 1, wherein the first porous material has a resistance to draw in a range from about 10 mm water to about 50 mm water and the second porous material has a resistance to draw in a range from about 1 mm water to about 3 mm water.

6. The inhaler article according to claim 1, wherein the central core portion forms about 50% or less of the diameter of the outer periphery layer.

7. The inhaler article according to claim 6, wherein the central core portion is formed of cellulose acetate material and the outer periphery layer is formed of polylactic acid material.

8. The inhaler article according to claim 1, wherein the central core portion forms greater than about 50% of the diameter of the outer periphery layer.

9. The inhaler article according to claim 8, wherein the central core portion is formed of polylactic acid material and the outer periphery layer is formed of cellulose acetate material.

10. The inhaler article according to claim 9, wherein the outer periphery layer comprises two or more apertures extending the length of the composite porous support element.

11. The inhaler article according to claim 1, wherein the air inlet region induces a vortex of inhalation airflow into the capsule cavity.

12. The inhaler article according to claim 1, wherein the outer periphery layer comprises two or more apertures extending the length of the composite porous support element.

13. The inhaler article according to claim 2, wherein the outer periphery layer comprises two or more apertures extending the length of the composite porous support element.

14. The inhaler article according to claim 3, wherein the outer periphery layer comprises two or more apertures extending the length of the composite porous support element.

15. The inhaler article according to claim 2, wherein the first porous material has a resistance to draw in a range from about 1 mm water to about 3 mm water and the second porous material has a resistance to draw in a range from about 10 mm water to about 50 mm water.

16. The inhaler article according to claim 3, wherein the first porous material has a resistance to draw in a range from about 1 mm water to about 3 mm water and the second porous material has a resistance to draw in a range from about 10 mm water to about 50 mm water.

17. An inhaler system comprising, the inhaler article according to claim 1, and a capsule disposed within the capsule cavity of the inhaler article, the capsule containing particles, the particles having a mass median aerodynamic diameter of about 5 micrometres or less.

18. The system according to claim 17, wherein the capsule contains particles comprising nicotine.

19. The system according to claim 17, wherein the capsule further contains a second population of flavour particles having a mass median aerodynamic diameter of about 20 micrometres or greater.

20. The system according to claim 17, wherein the system further comprises a piercing element removably engageable with the inhaler article to activate the capsule and wherein the endpiece element is configured to be pierced by the piercing element when activating the capsule.

* * * * *